(12) United States Patent
Hoover

(10) Patent No.: US 10,610,424 B1
(45) Date of Patent: Apr. 7, 2020

(54) BANDAGE DISPENSER

(71) Applicant: Robert L. Hoover, Saint Cloud, MN (US)

(72) Inventor: Robert L. Hoover, Saint Cloud, MN (US)

( * ) Notice: Subject to any disclaimer, the term of this patent is extended or adjusted under 35 U.S.C. 154(b) by 224 days.

(21) Appl. No.: 15/657,436

(22) Filed: Jul. 24, 2017

Related U.S. Application Data

(63) Continuation-in-part of application No. 13/213,056, filed on Aug. 18, 2011, now Pat. No. 9,751,674.

(60) Provisional application No. 61/458,857, filed on Dec. 3, 2010.

(51) Int. Cl.
*A61F 13/551* (2006.01)

(52) U.S. Cl.
CPC .. *A61F 13/551* (2013.01); *A61F 2013/55195* (2013.01)

(58) Field of Classification Search
CPC .. A61F 13/0203; A61F 15/001; A61F 13/551; B65D 75/327; Y10S 206/82
USPC ......... 206/440–441; 602/57, 41, 43; 211/113
See application file for complete search history.

(56) References Cited

U.S. PATENT DOCUMENTS

| | | | | |
|---|---|---|---|---|
| 2,005,676 A | * | 6/1935 | Hanover ............... | A61F 15/002 206/441 |
| 2,035,196 A | * | 3/1936 | Schiek .................. | B65D 75/04 206/441 |
| 4,666,040 A | * | 5/1987 | Murata ................ | B65D 75/327 206/232 |
| 4,807,753 A | * | 2/1989 | Goldstein ............. | A61F 15/002 206/390 |
| 5,981,823 A | * | 11/1999 | Turngren ............ | A61F 13/0279 206/440 |
| 6,140,549 A | * | 10/2000 | Pompei, Jr. ........... | A61F 15/001 206/440 |
| 6,225,522 B1 | * | 5/2001 | Schroeder ............. | A61F 15/001 602/57 |
| 7,445,142 B2 | * | 11/2008 | Salani ................... | A61F 15/001 206/102 |
| 7,753,204 B2 | * | 7/2010 | Grossman ............. | A61F 15/001 206/440 |
| 8,528,730 B2 | * | 9/2013 | Grossman ............. | A61F 15/001 206/440 |
| 2004/0099626 A1 | * | 5/2004 | Belt ...................... | A47F 5/0006 211/113 |

(Continued)

*Primary Examiner* — Chun Hoi Cheung
(74) *Attorney, Agent, or Firm* — Albert W. Watkins

(57) ABSTRACT

A bandage dispenser has a mounting strip supporting a plurality of partially overlapping bandage packages. Each package individually wraps a bandage. Each bandage package has a bifurcated opening, with one half of the bifurcated opening bonded to the mounting strip and the second half of the bifurcated opening folded away from the mounting strip to facilitate manual grasping. A person one-handedly grasps the second half of the bifurcated opening and pulls away from the mounting strip to open the bandage package. Using the same single hand, the person may release the bifurcated opening, and then grasp and remove the sterile bandage from the package. Once the bandage has been applied, a person may again use a single hand to finish tearing the bandage package from the mounting strip, revealing the next bandage package bifurcated opening. Optional pockets provide tactile feedback and reduce the chance of accidentally spilling a bandage.

20 Claims, 7 Drawing Sheets

(56) References Cited

U.S. PATENT DOCUMENTS

2006/0169616 A1\* 8/2006 Auger ................... A61F 15/001
                                                          206/441
2013/0256171 A1\* 10/2013 Kerdemelidis ....... A61F 15/001
                                                          206/441

\* cited by examiner

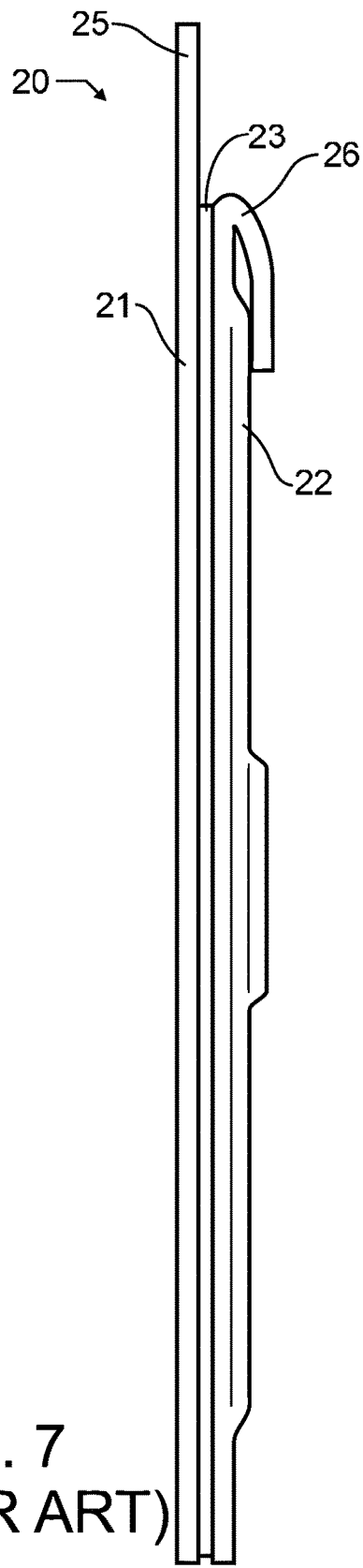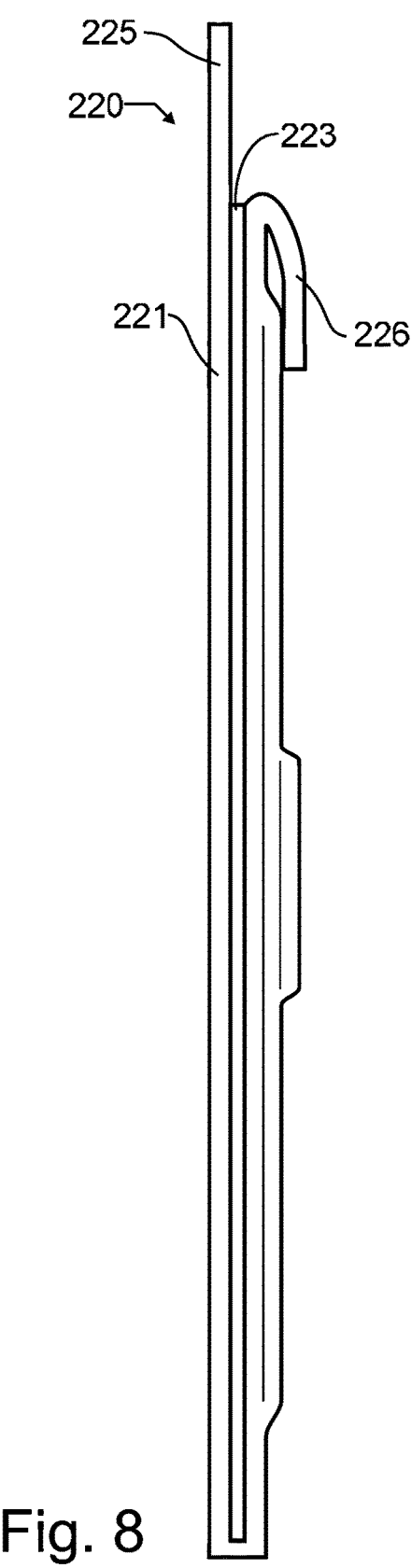
Fig. 7
(PRIOR ART)
Fig. 8

BANDAGE DISPENSER

CROSS REFERENCE TO RELATED APPLICATIONS

The present application is a Continuation-In-Part of U.S. patent application Ser. No. 13/213,056 filed Aug. 18, 2011, which in turn claims the benefit of U.S. provisional patent application 61/458,857 filed Dec. 3, 2010, each of like title and inventorship, the teachings and entire contents which are incorporated herein by reference.

BACKGROUND OF THE INVENTION

1. Field of the Invention

The present invention pertains generally to special receptacles or packages for body treatment articles, and more particularly to a package displaying a plurality of individually prepackaged adhesive bandages that may individually be removed and unwrapped with a one-hand single motion.

2. Description of the Related Art

Bandages have likely been used since before recorded history, and have also undoubtedly been fashioned from many different materials. However, since the popular identification of micro-organisms by the likes of Louis Pasteur, there has been an ever-increasing awareness, albeit gradually, in the medical field of the importance of sterility in the care and treatment of wounds. For a time in relatively recent history, more and better antibiotics and cleansers were developed that facilitated the creation of a sterile environment, even without a wound being perfectly clean or a bandage being sterile. However, particularly recently there have been several bacteria that have developed resistance to most or even all of the known antibiotic treatments. Consequently, health care professionals today cannot rely solely on antibiotics. With every passing day, the importance of a sterile treatment environment, sterile wound cleansing, and sterile bandages increases.

One benefit of this recognition has been the improved packaging of bandages, so that most modern bandages are produced in a sterile environment and are individually wrapped to protect and preserve each bandage. Very commonly, individually wrapped sterile bandages may also be provided with adhesive tape, and are popularly sold, for example, under the Band-Aids™ brand. These individually wrapped sterile bandages are produced and then further packaged in a paperboard box or a metal container, both which will typically use a hinged closure flap to fully enclose and protect the individually wrapped sterile bandages during storage.

The retrieval of bandages from storage is always fraught with challenges. When the need for a bandage arises, first the container of bandages must be located and retrieved from storage and opened. There are many different styles of bandages, and the contents of a particular paperboard or metal container is generally not clear or certain until the container is opened. Much inconvenience arises when the container is opened, only for the person to discover that the supply of bandages needed to treat a particular wound have already been exhausted and not restocked. Furthermore, the opening of the container in many cases requires or is greatly facilitated by the use of two hands.

In the event of good fortune, where a properly sized individually wrapped sterile bandage is located, then the subsequent application and use of the individual bandage presents further challenge. First, the bandage must be separated from the individual wrapper. Many bandages today have a bifurcated end on the bandage wrapper, where the top and bottom sheets that together form the bandage wrapper are separated. A person will grasp each sheet separately, with one sheet in each hand, and then pull the two sheets apart to reveal the bandage enclosed therein. Once again, this requires or is greatly facilitated by the use of two hands.

Since there are several steps that require the use of two hands, a person who is wounded may often times be unable to access an individual bandage. Likewise, in a health care facility, a health-care provider such as a doctor or nurse may have only one hand available, and so again at those times will be unable to access an individual bandage. Instead, the health care provider will have to request and wait for another provider to assist.

Others have developed a variety of bandage dispensers to try to improve upon the existing paperboard box or metal containers. Exemplary patents, the teachings and contents which are incorporated herein by reference, include U.S. Pat. No. 2,133,609 by Eustis, entitled "Surgical dressing"; U.S. Pat. No. 2,965,223 by Schladermundt et al, entitled "Dispenser pack of individual adhesive bandages"; U.S. Pat. No. 5,511,689 by Frank, entitled "Dispensing device for adhesive-backed articles"; and U.S. Pat. No. 6,079,190 by Simpson, entitled "Bandage package and method of dispensing". While these patents offer significant improvement over the prior art containers, and offer high density packaging of bandages, none offer a preferred combination of one-handed manual access and opening of individual wrappers, visual assessment of supply stock from a distance; and a sterile individual wrapper.

In addition to the aforementioned patents, Webster's New Universal Unabridged Dictionary, Second Edition copyright 1983, is incorporated herein by reference in entirety for the definitions of words and terms used herein.

SUMMARY OF THE INVENTION

In a first manifestation, the invention is a bandage dispenser, having a generally planar bandage dispenser substrate and at least one row of partially overlapping individually wrapped sterile bandages mounted onto a dispensing region within the generally planar bandage dispenser substrate. Each one of the individually wrapped sterile bandages are bifurcated at one end and have a first sheet defining a top portion of the wrapper, and a second sheet defining the opposed bottom portion of the wrapper. A bond adheres a one of the first and second sheets to the generally planar bandage dispenser substrate.

OBJECTS OF THE INVENTION

Exemplary embodiments of the present invention solve inadequacies of the prior art by providing a generally planar bandage dispenser having at least one row of partially overlapping individually wrapped sterile bandages. Each of the individually wrapped sterile bandages are adhered on one surface of a bifurcated wrapper to the generally planar bandage dispenser.

A first object of the invention is to package a plurality of individually packaged sterile bandages into a single display unit. A second object of the invention is to enable a person to visually determine the quantity of sterile bandages instantaneously at a significant distance from the single display unit. Another object of the present invention is to facilitate the removal of individual bandages from their individual sterile packages using only a single hand, without any risk to the sterility of the bandage being removed. A further object of the invention is to provide a high density display unit displaying many individually packaged sterile bandages in a small space. Yet another object of the present invention is to enable the single display unit to be populated with individually packaged sterile bandages immediately subsequent to the production and packaging of individually packaged sterile bandages, preferably in a way that permits automation of the populating. Another object of the invention is the provision of a low-cost single display unit. A further object of the invention is for the use of the single display unit to be intuitive, and so be immediately used by most persons without consequential training being required.

BRIEF DESCRIPTION OF THE DRAWINGS

The foregoing and other objects, advantages, and novel features of the present invention can be understood and appreciated by reference to the following detailed description of the invention, taken in conjunction with the accompanying drawings, in which:

FIG. 7 illustrates a prior art packaged bandage as used and illustrated in the preferred and first alternative embodiment bandage dispensers of FIGS. 1-6 from a side view similar to that of FIGS. 2 and 5.

FIG. 8 illustrates a first alternative embodiment packaged bandage designed in accord with the teachings of the present invention from a front plan view.

DESCRIPTION OF THE PREFERRED EMBODIMENT

Figure 6:
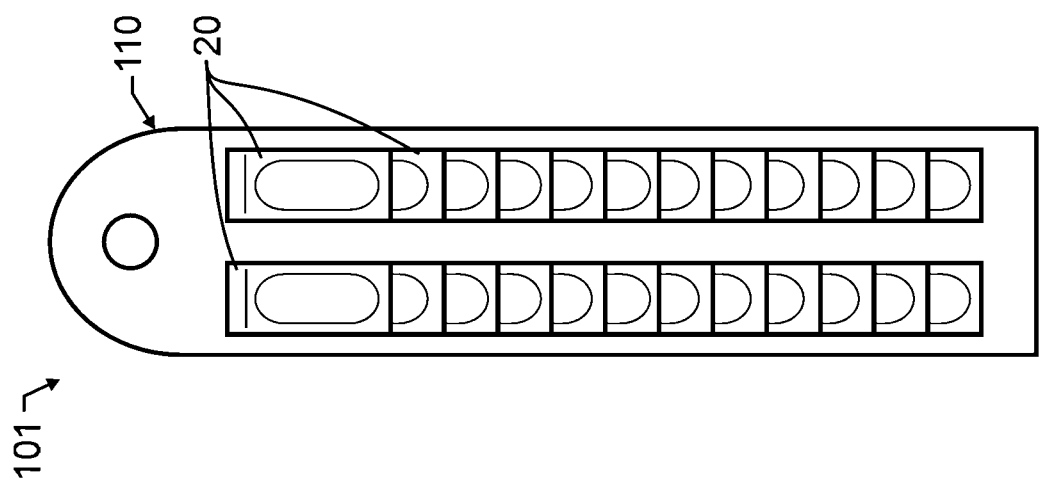
FIG. 6 illustrates a first alternative embodiment bandage dispenser designed in accord with the teachings of the present invention from a front plan view.

Bandage dispenser 1 is illustrated for exemplary purposes in FIGS. 1-5, and includes a generally planar bandage dispenser substrate 10. At least one row of partially overlapping individually wrapped sterile bandages 20 are mounted onto a dispensing region 12. An optional mounting region 14 in the preferred embodiment bandage dispenser 1 is provided with a hanging hole 16 suitable for hanging from a nail or other protrusion extending from a surface. Other mounting structures besides or in addition to hanging hole 16 are further contemplated herein, and may include, for exemplary purposes only and not limiting solely thereto, magnets, hook-and-loop fasteners such as Velcro™, temporary or permanent adhesives, and any other suitable apparatus or fasteners known in the fastener and mounting arts. These mounting structures or fasteners may be provided in optional mounting region 14, or may alternatively be coatings or backings provided on a major surface of generally planar bandage dispenser substrate 10 opposed to the major surface to which individually wrapped sterile bandages 20 are mounted.

Substrate 10 in the preferred embodiment is fabricated from plastic sheet that is pliable, but which has sufficient rigidity to resist substantial deformation when an individually wrapped sterile bandage 20 is opened one-handedly. Nevertheless, any suitable material may be selected, depending upon the needs of a designer and price and availability of material. Exemplary alternative materials include wood, cardboard, paperboard, paper, laminates, composites or any other suitable materials.

Figure 1:
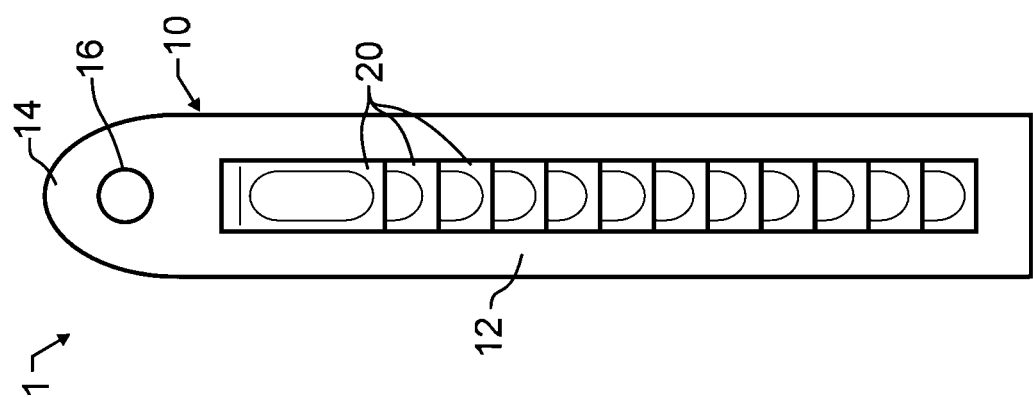
FIG. 1 illustrates a preferred embodiment bandage dispenser designed in accord with the teachings of the present invention from a front plan view.

Most preferably, individually wrapped sterile bandages 20 overlap partially but not completely with adjacent individually wrapped sterile bandages 20 to increase the density of available bandages. Because bandages 20 do not totally overlap with each other, and instead only partially overlap, then based upon the total extent of overlapped bandages 20, such as the vertical extent of bandages 20 as illustrated in FIG. 1, a person can reasonably visually discern from a significant distance beyond arm's reach approximately how many bandages remain.

Figure 3:
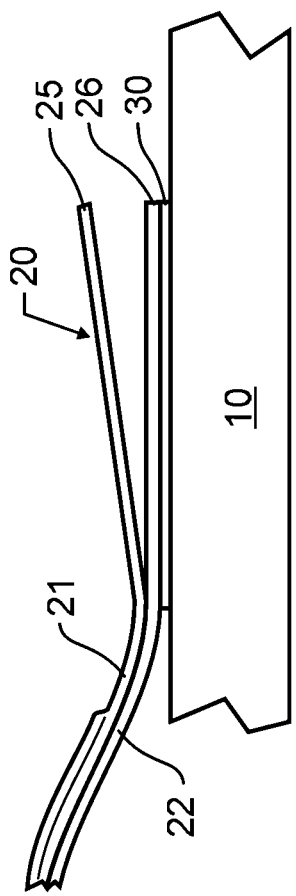
FIG. 3 illustrates a side sectional view of the preferred embodiment bandage dispenser of FIG. 2 taken along line 3'.
Figure 4:
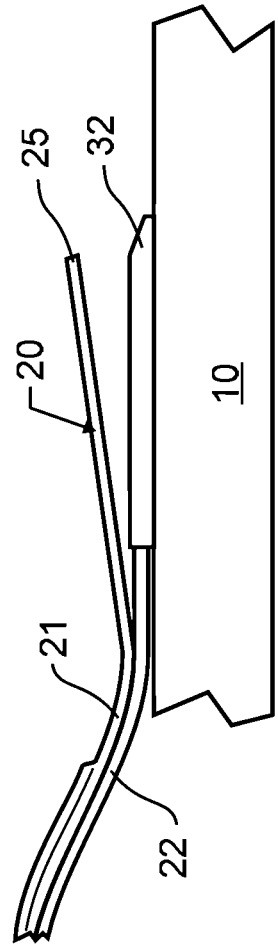
FIG. 4 illustrates a side sectional view of a first alternative embodiment bandage dispenser from the same view as that of FIG. 3.

Individually wrapped sterile bandages 20 will most preferably be bifurcated at one end, as is commonly known in the adhesive bandage art and illustrated herein in FIGS. 3 and 4. A first sheet 21 may serve as a top portion of the wrapper, and a second sheet 22 may define the opposed bottom portion of the wrapper, where the references to top and bottom are understood to be interchangeable. As illustrated in FIG. 3, second sheet 22 is preferably adhered to generally planar bandage dispenser substrate 10 through a bond 30. Bond 30 may be formed from an adhesive, such as a Pressure-Sensitive Acrylic (PSA), a moisture sensitive adhesive, various cements, thermally activated or Ultra-Violet (UV) cured adhesives, or any other adhesive or alternative to an adhesive. The adhesive is not critical to the present invention, and may comprise an adhesive applied to either second sheet 22 or to generally planar bandage dispenser substrate 10 prior to attachment therebetween. Further, the particular technique for applying the adhesive is not critical to the present invention, and so for exemplary purposes only, may include such techniques as roll or contact applicators, screen printing, spraying, ink jet or thermal transfer, or any other suitable technique. Alternatives to adhesives include, for exemplary purposes only and not limiting solely thereto, such techniques as thermal bonding, friction welding or ultrasonic welding, either directly between second sheet 22 and generally planar bandage dispenser substrate 10, or through some intermediate layer that may provide desired bonding characteristics, processes or handling.

FIG. 4 illustrates another alternative embodiment, using the same numbering as found in FIG. 3, but instead of bond 30, a tape 32 may be applied over second sheet 22, thereby securing second sheet 22 to substrate 10. As illustrated in FIG. 4, and if so desired, tape 32 may be applied over bifurcated end 26, and may or may not wrap from a front major surface of generally planar bandage dispenser substrate 10 to a minor surface or to the back major surface, depending upon the wishes and needs of a designer.

Figure 5:
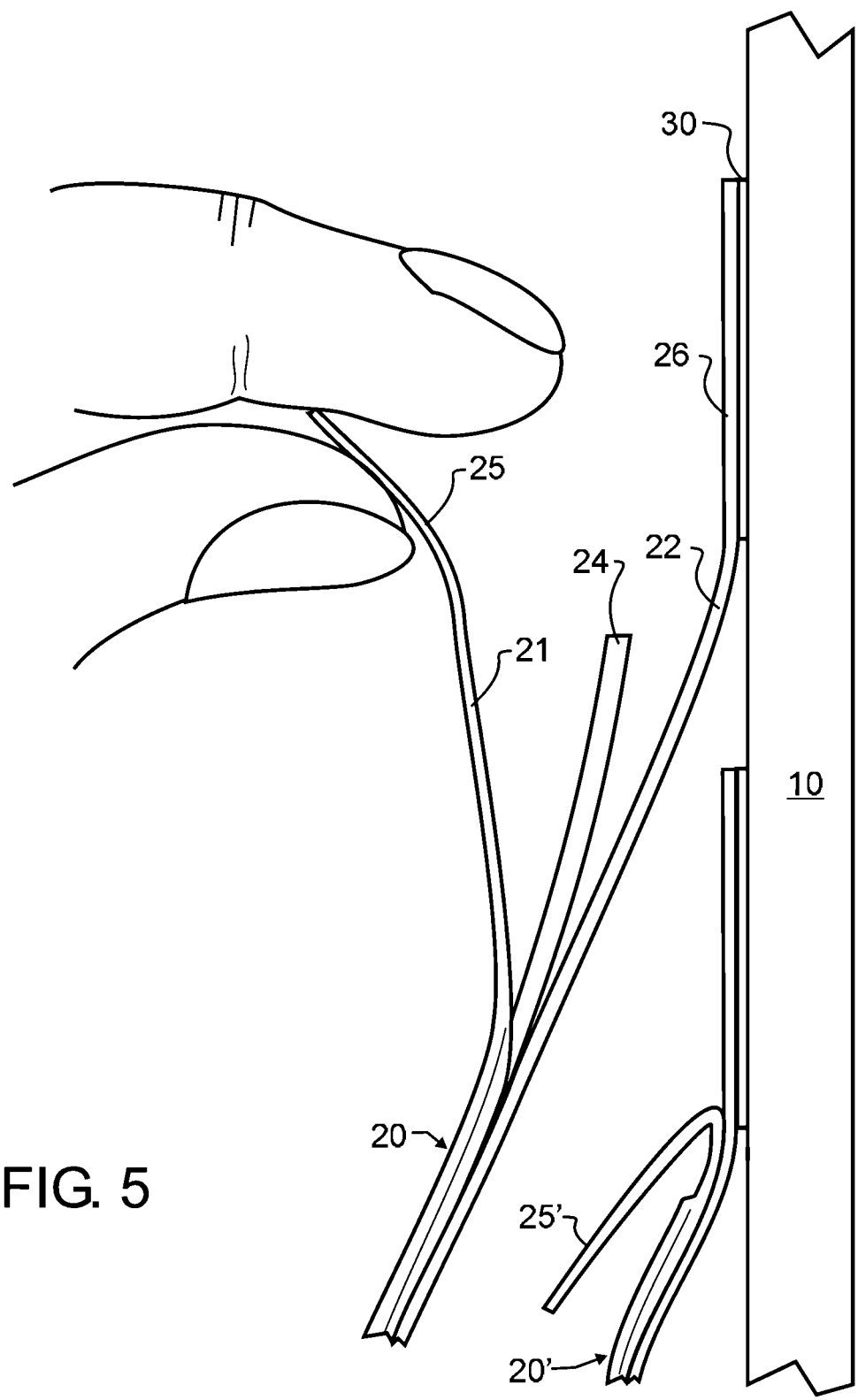
FIG. 5 illustrates the preferred embodiment bandage dispenser of FIG. 1 from an enlarged side section view similar to that of FIG. 3, but illustrating two overlapping bandages and illustrating the partial removal of one of the bandages.

As illustrated in FIG. 5, each of the individually wrapped sterile bandages 20 are adhered on one surface of a bifurcated wrapper end 26 to the generally planar bandage dispenser substrate 10. While in the prior art this bifurcated wrapping is designed to be grasped with one hand at each one of bifurcated wrapper ends 25, 26, owing to bond 30 or the equivalent, a person may simply grasp a single wrapper end with a single hand, such as end 25 as illustrated in FIG. 5, and then peel bifurcated wrapper end 25 down and away from bifurcated end 26, thereby further separating top layer 21 from bottom layer 22 and releasing bandage 24, which may be an adhesive bandage or bandage without adhesive, from bifurcated wrapper ends 25, 26. Once sufficiently released, bandage 24 may then be grasped with the same hand that separated top layer 21 from bottom layer 22, and then subsequently applied to a wound.

In the preferred embodiment illustrated in FIG. 5, when uppermost individually wrapped sterile bandage 20 is opened and bandage 24 removed therefrom, then bifurcated end 26 may preferably be forcibly detached from substrate 10. As may be apparent, substrate 10 will most preferably be sufficiently more durable than at least one of bifurcated end 26 or bond 30 that any failure occurs only in either bifurcated end 26 or bond 30, thereby only separating uppermost individually wrapped sterile bandage 20 from substrate 10. Once uppermost individually wrapped sterile bandage 20 has been separated, individually wrapped sterile bandage 20' becomes the new uppermost individually wrapped sterile bandage. To better facilitate manual grasping, in the preferred embodiment illustrated in FIG. 5, at least the second and subsequent individually wrapped sterile bandages 20' may also have the bifurcated end 25' that is not attached to substrate 10 folded downward and outward from substrate 10.

Various embodiments of apparatus designed in accord with the present invention have been illustrated in the various figures. The embodiments are distinguished by the hundreds digit, and various components within each embodiment designated by the ones and tens digits. However, many of the components are alike or similar between embodiments, so numbering of the ones and tens digits have been maintained wherever possible, such that identical, like or similar functions may more readily be identified between the embodiments. If not otherwise expressed, those skilled in the art will readily recognize the similarities and understand that in many cases like numbered ones and tens digit components may be substituted from one embodiment to another in accord with the present teachings, except where such substitution would otherwise destroy operation of the embodiment. Consequently, those skilled in the art will readily determine the function and operation of many of the components illustrated herein without unnecessary additional description.

FIG. 6 illustrates a first alternative embodiment bandage dispenser 101. This dispenser 101 shows that the particular geometry of substrates 10, 110 are not critical to the present invention, and so a plurality of rows of partially overlapped individually wrapped sterile bandages 20 may be provided.

Since in the preferred and alternative embodiments illustrated in the Figures and described herein each bond 30 is at a predictable and repeatable spacing from the next previous bond, each bond and each individually wrapped sterile bandage 20 may be placed or formed using automated assembly equipment. Consequently, preferred embodiment bandage dispenser 1 may be produced by populating generally planar bandage dispenser substrate 10 with individually wrapped sterile bandages 20 immediately subsequent to the production and packaging of individually packaged sterile bandages 20, preferably in a way that permits automation of the populating. The resulting bandage dispenser 1 is a low-cost display unit that is intuitive to use by most persons without consequential training.

Figure 2:
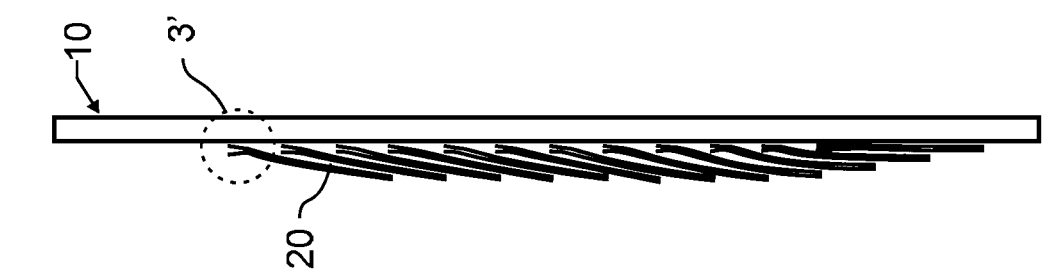
FIG. 2 illustrates the preferred embodiment bandage dispenser of FIG. 1 from a side plan view.

FIG. 7 illustrates a prior art packaged bandage as used and illustrated in the preferred and first alternative embodiment bandage dispensers of FIGS. 1-6 from a side view similar to that of FIGS. 2 and 5. Noteworthy herein is that first sheet 21 and second sheet 22 are secured to each other using an adhesive 23 or the like. This illustration is provided for reference to the illustrations of FIGS. 8 and 9 that illustrate alternative embodiment packaged bandages designed in accord with the teachings of the present invention.

FIG. 8 illustrates a first alternative embodiment packaged bandage 200 having a single sheet 221 that is folded into a "U" shape, and which is held together on three of the four edges with adhesive 223. As a result, the two distal terminations of sheet 221 define the two bifurcated wrapper ends 225, 226. The use of a single sheet 221 increases the likelihood that there may remain a small pocket at the bottom, distal to bifurcated wrapper ends 225, 226 when a person pulls bifurcated wrapper end 226 away from end 225. This pocket will then retain a bandage 24 within, further facilitating one-handed opening and removal of bandage 24 from within sheet 221.

Figure 9:
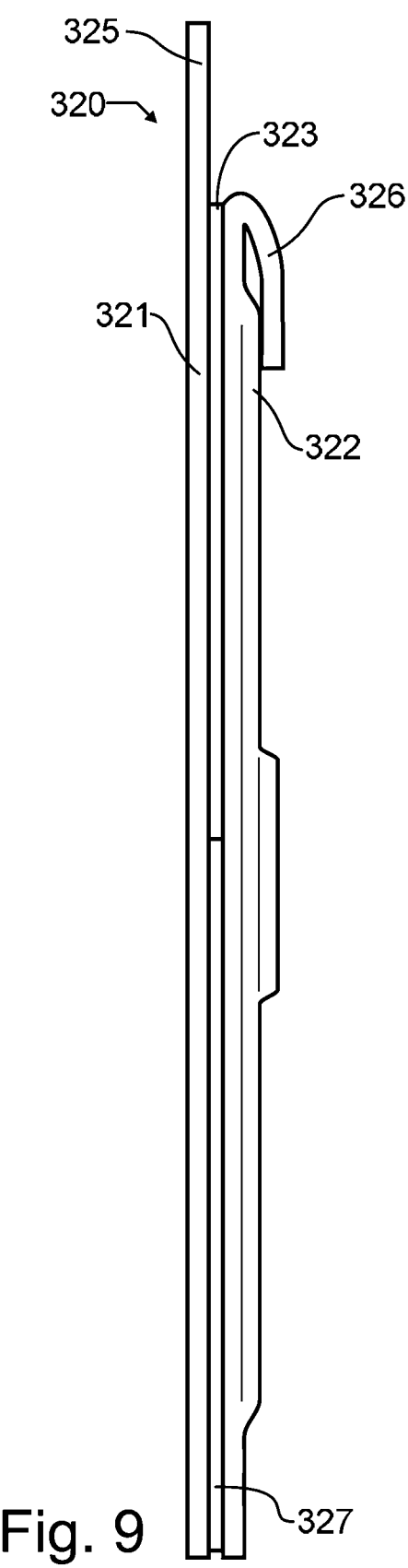
FIG. 9 illustrates a second alternative embodiment packaged bandage designed in accord with the teachings of the present invention from a front plan view.

FIG. 9 illustrates a second alternative embodiment packaged bandage 320 designed in accord with the teachings of the present invention. In this alternative embodiment, single adhesive 23 has been replaced by two different adhesives 323, 327. Most preferably, adhesive 323 will have a sufficiently low adhesive strength that it will allow sheets 321, 322 to separate from each other when a relatively small pulling force is manually applied to bifurcated wrapper end 326. This allows sheet 322 to be easily manually separated from sheet 321 in the regions held together by adhesive 323. In order to achieve this desired manual separation, either the adhesion of adhesive 323 to one or both of sheets 321, 322 must be lower than the ultimate tensile strength of sheets 321, 322, or the internal cohesion within adhesive 323 must be lower.

Adhesive 327 is selected to have a greater adhesive strength than that of adhesive 323. Once sheet 322 is fully separated from sheet 321 in those regions previously held together by adhesive 323, then sheets 321, 322 will be more securely bonded. As illustrated in FIG. 9, this is some lower portion of packaged bandage 320, which will form a pocket that will tend to retain bandage 24 therein. In second alternative embodiment packaged bandage 320, adhesive 327 is preferably not manually separable in the regions of adhesive 327 without potentially exceeding the ultimate tensile strength of sheets 321, 322. In a different alternative embodiment, adhesive 327 provides an adhesive strength less than the ultimate tensile strength of sheets 321, 322, but still greater than the adhesive strength of adhesive 323. As long as adhesive 327 provides greater adhesive strength than adhesive 323, second alternative embodiment packaged bandage 320 will allow a person to manually open packaged bandage 320 while not accidentally spilling bandage 24 therefrom. This is accomplished by providing distinctive tactile feedback when the separation between sheets 321 and 322 transitions from adhesive 323 to adhesive 327.

Figure 10:
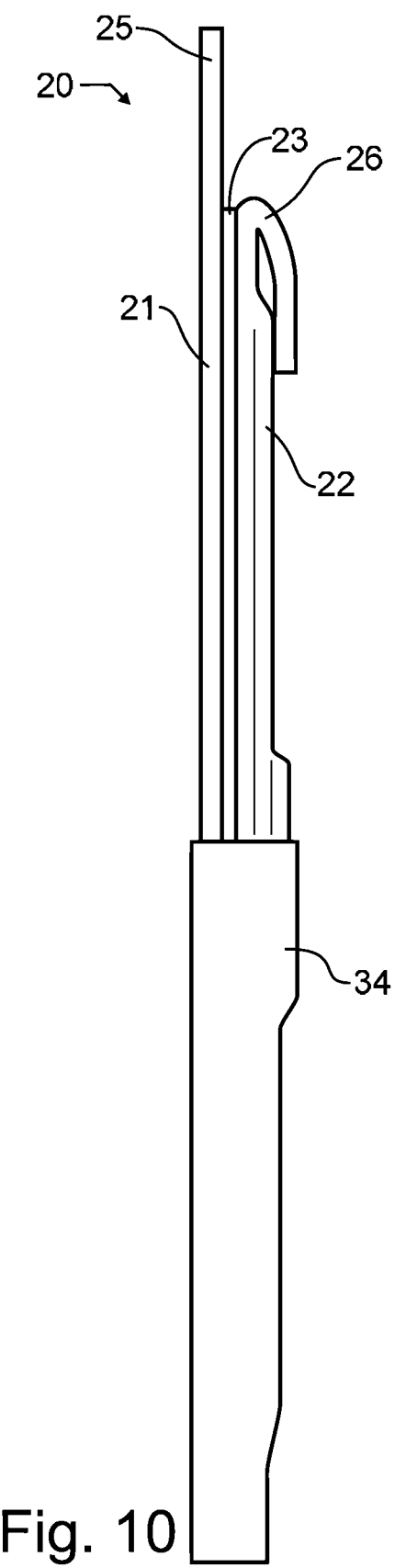
FIG. 10 illustrates a third alternative embodiment packaged bandage designed in accord with the teachings of the present invention from a front plan view.

FIG. 10 illustrates a preferred embodiment packaged bandage 20 in further combination with a secondary pocket 34 that encompasses some lower portion of packaged bandage 20. This combination defines a third alternative embodiment packaged bandage having the distinctive manual feedback offered by second alternative embodiment packaged bandage 320, while still using a standard production individually wrapped sterile bandage 20.

Figure 11:
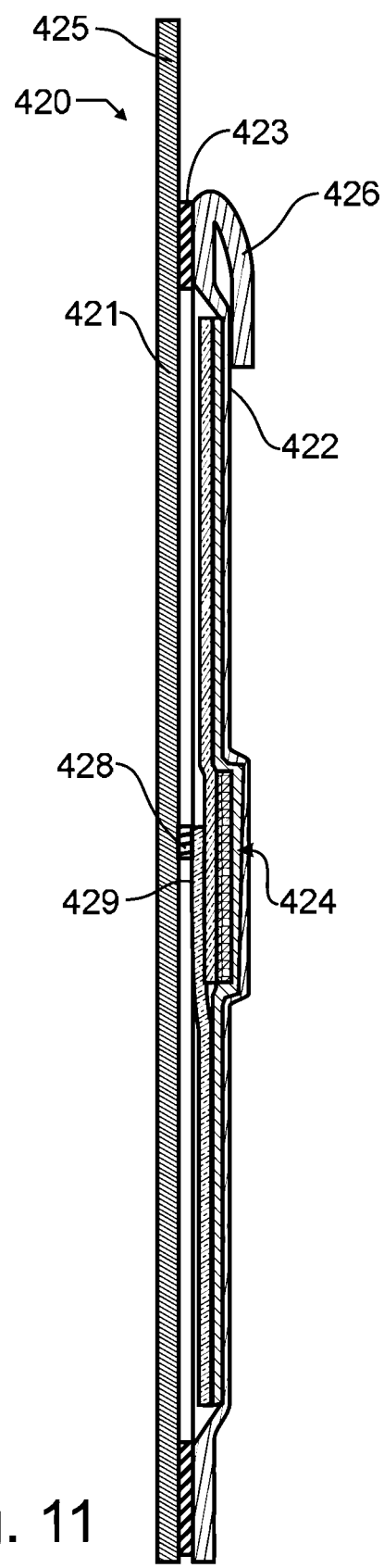
FIG. 11 illustrates a fourth alternative embodiment packaged bandage designed in accord with the teachings of the present invention from a side section view.

FIG. 11 illustrates a fourth alternative embodiment packaged bandage 420 designed in accord with the teachings of the present invention. In this embodiment, the prior art individually wrapped sterile bandage 20 of FIG. 7 has been modified by the addition of a dot 428 of an adhesive is used to at least partially secure the outer wax or release paper strip 429 to first sheet 421. Dot 428 may comprise a spot, stripe or equivalent, the geometry which is not critical to the present invention. The adhesive will most preferably be a tacky composition which has adequate adherence to release paper that otherwise is difficult to adhere to. In such instance, a silicone adhesive gel may be used. In a further alternative, the face of wax or release paper strip 429 facing away from bandage 424 and toward sheet 421 may be configured to be free of a release coating, thereby increasing the adhesion with various adhesives, and thereby also increasing the selection of adhesives that will adhere thereto.

Adhesive dot 428 causes release paper strip 429 to be removed from bandage 424 when bandage 424 is removed from between sheets 421, 422. To remove bandage 424, a person will first pull bifurcated wrapper end 426 down and away from bifurcated wrapper end 425, causing adhesive 423 to separate, similar in operation to adhesive 323. This can easily be done using only one hand. When bifurcated wrapper end 426 and sheet 422 have been sufficiently removed from sheet 421 to adequately reveal bandage 424, then a person will next grasp the accessible portion of bandage 424. When the person pulls on bandage 424 to remove it from the pocket that remains between sheets 421, 422, adhesive dot 428 will retain release paper strip 429, thereby starting the opening of bandage 424. When bandage 424 has been fully removed from the pocket between sheets 421, 422, outer release paper strip 429 will be left behind, adhered to sheet 421. This leaves the adhesive on the lowermost one of the two adhesive strips that define bandage 424 exposed, allowing the person to then immediately apply bandage 424 to a wound using a single hand by pressing the exposed adhesive strip against the skin, without requiring any further manipulation.

While sheet 422 might in the above description be only partially removed to define an open pocket with sheet 421, this is not essential. Instead, if sheet 422 has been completely removed, then adhesive dot 428 will tend to hold bandage 424 in place, thereby reducing the likelihood of accidentally dropping and contaminating the bandage. After sheet 422 has been fully removed, and as before, the person will then pull on bandage 424 to remove it from sheet 421. Adhesive dot 428 will retain release paper strip 429 to sheet 421, thereby starting the opening of bandage 424. When bandage 424 has been fully removed from sheet 421, the lowermost one of the two adhesive strips that define bandage 424 will be exposed, allowing the person to then immediately apply bandage 424 to a wound, without requiring any further manipulation.

Figure 12:
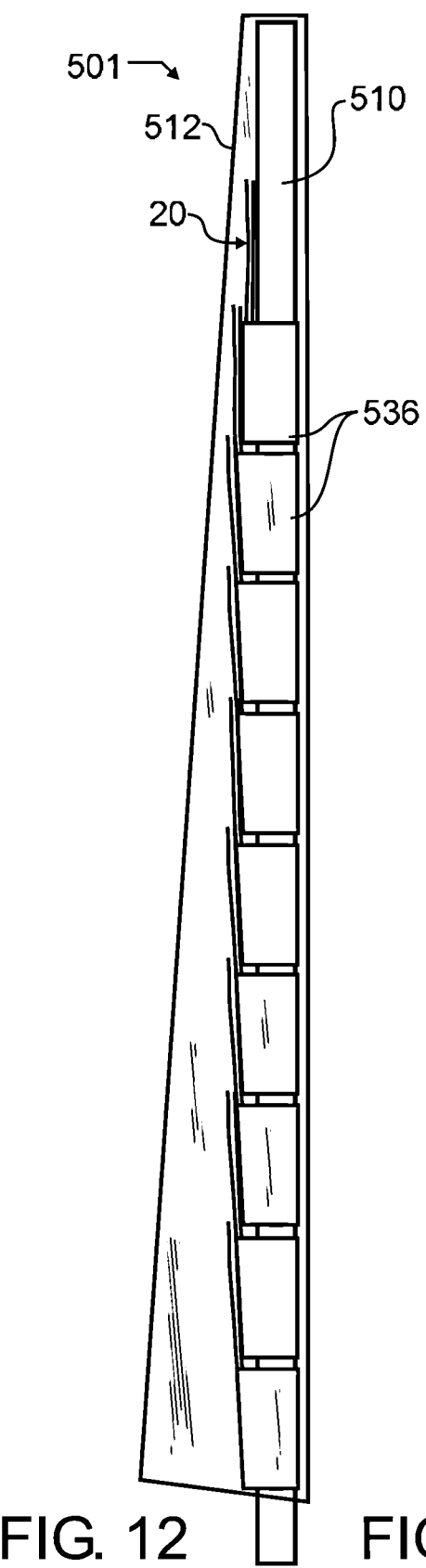
FIG. 12 illustrates a second alternative embodiment bandage dispenser designed in accord with the teachings of the present invention from a side plan view.
Figure 13:
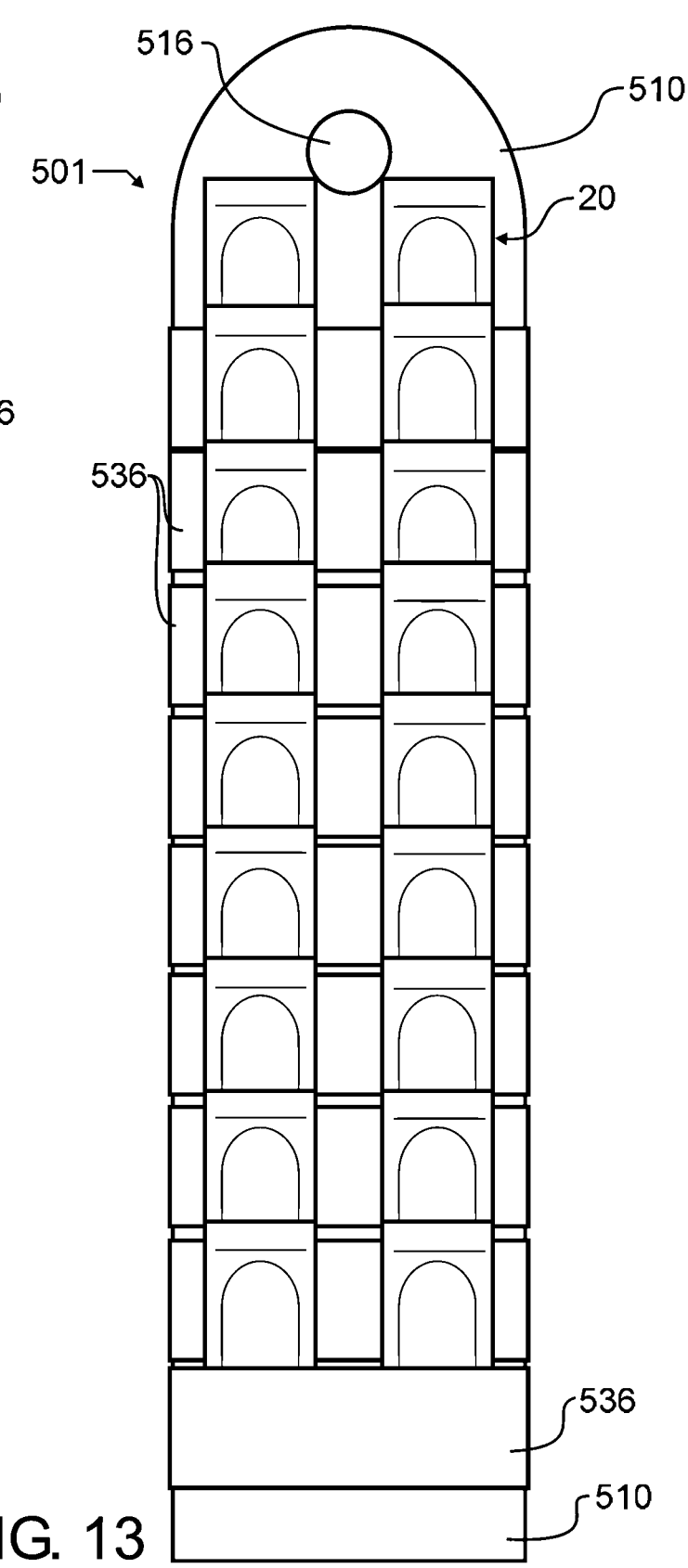
FIG. 13 illustrates the second alternative embodiment bandage dispenser of FIG. 12 from a front plan view.

FIGS. 12 and 13 illustrate a second alternative embodiment bandage dispenser 501, which includes a plurality of wraps 536 that form pockets to encompass the lower portion of each individually wrapped sterile bandage 20. These wraps are preferably adhered to the generally planar bandage dispenser substrate 510. In this second alternative embodiment 501, they fully encircle or circumscribe substrate 510. However, in further alternative embodiments, these wraps only partially circumscribe substrate 510, or in an even further alternative embodiment are adhered solely to the top surface of substrate 510. Irrespective of how extensively they wrap about substrate 510, wraps 536 are nevertheless secured to substrate 510 sufficiently to allow a person to open individually wrapped sterile bandages 20 as described herein above in other embodiments, by pulling down on bifurcated wrapper end 25 and thereby separating first sheet 21 from second sheet 22. Rather than fully separating the two sheets, when sheet 21 is partially separated from sheet 22 it will engage with wrap 536. At such point, sheet 21 will no longer non-destructively separate further, and a person will receive tactile feedback. They will know then to remove bandage 24 from between sheets 21 and 22.

A secondary covering 512, such as a clear plastic sheet bonded at a top near to hole 516, and hanging down therefrom, may optionally be provided to gain additional protection against accidental or unintentional spraying or other contamination of individually wrapped sterile bandages 20. A person accessing individually wrapped sterile bandages 20 will slide their hand under the secondary covering and lift to access an individually packaged sterile bandage.

While the foregoing details what is felt to be the preferred embodiment of the invention, no material limitations to the scope of the claimed invention are intended. Further, features and design alternatives that would be obvious to one of ordinary skill in the art are considered to be incorporated herein. The scope of the invention is set forth and particularly described in the claims herein below.

I claim:
1. A bandage dispenser, comprising:
a generally planar bandage dispenser substrate;
at least one row of partially overlapping individually wrapped sterile bandages mounted onto a dispensing region within said generally planar bandage dispenser substrate, each one of said individually wrapped sterile bandages bifurcated at one end and having a first sheet defining a top portion of the wrapper, and a second sheet defining the opposed bottom portion of the wrapper, said first sheet adhered to said second sheet using a first adhesive to define a sealed compartment containing a sterile bandage therein and unadhered at said one end to define said bifurcation; and
each one of said partially overlapping individually wrapped sterile bandages second sheet bifurcated ends adhered to said generally planar bandage dispenser substrate through a second-sheet-to-substrate bond stronger than said first adhesive and thereby adapted to adhere said second sheet bifurcated end to said generally planar bandage dispenser during separation of said first sheet from said second sheet, said generally planar bandage dispenser substrate more durable than said second-sheet-to-substrate bond, said second-sheet-to-substrate bond thereby adapted to release said second sheet from said generally planar bandage dispenser substrate upon application of a separation force applied subsequent to a separation of said first sheet from said second sheet;

an uppermost one of said partially overlapping individually wrapped sterile bandages bifurcated end exposed; and each one of said partially overlapping individually wrapped sterile bandages bifurcated ends subsequent to said uppermost one concealed between a next adjacent and relatively more upper one of said partially overlapping individually wrapped sterile bandages and said generally planar bandage dispenser substrate.

2. The bandage dispenser of claim 1, wherein said generally planar bandage dispenser substrate further comprises a mounting region provided with a mounting structure for coupling to diverse apparatus.

3. The bandage dispenser of claim 2, wherein said mounting structure further comprises a fastener provided on a first major surface of said generally planar bandage dispenser substrate opposed to a second major surface to which said individually wrapped sterile bandages are bonded.

4. The bandage dispenser of claim 1, wherein said generally planar bandage dispenser substrate further comprises sheet stock.

5. The bandage dispenser of claim 4, wherein said generally planar bandage dispenser substrate further comprises pliable sheet stock which has sufficient rigidity to resist substantial deformation when an individual one of said at least one row of partially overlapping individually wrapped sterile bandages is opened one-handedly.

6. The bandage dispenser of claim 4, wherein said generally planar bandage dispenser substrate further comprises plastic sheet stock.

7. The bandage dispenser of claim 1, wherein said bond further comprises an adhesive.

8. The bandage dispenser of claim 1, wherein said bond further comprises thermal bonding.

9. The bandage dispenser of claim 1, wherein said bond further comprises friction welding.

10. The bandage dispenser of claim 1, wherein said bond further comprises ultrasonic welding.

11. The bandage dispenser of claim 1, wherein said bond further comprises a tape.

12. The bandage dispenser of claim 1, wherein said at least an individual one of said at least one row of partially overlapping individually wrapped sterile bandages has a first sheet portion of said bifurcated end folded away from said generally planar bandage dispenser substrate to form an obtuse angle with a second sheet portion of said bifurcated end which thereby facilitates manual grasping.

13. The bandage dispenser of claim 1, further comprising a plurality of rows of partially overlapped individually wrapped sterile bandages.

14. The bandage dispenser of claim 1, wherein each bond is provided at a predictable and repeatable spacing from an adjacent bond, wherein said bonds may be placed or formed using automated assembly equipment.

15. The bandage dispenser of claim 1, wherein each one of said individually wrapped sterile bandages further comprises:
a pair of adhesive strips extending from a bandage pad having a non-adhesive first major surface and an adhesive second major surface;
a pair of adhesive release paper strips, each one of said pair of adhesive release paper strips adhered to a one of said pair of adhesive strip second major surfaces and configured to enclose said adhesive layer between said non-adhesive first major surface and said adhesive release paper strip;
further comprising an adhesive dot affixing a one of said pair of adhesive release paper strips to said second sheet.

16. The bandage dispenser of claim 1, further comprising at least one pocket at least partially circumscribing at least one of said individually wrapped sterile bandages, said at least one pocket located distal to said bifurcated end and extending incompletely thereto.

17. The bandage dispenser of claim 16, wherein said at least one pocket further comprises a plurality of wraps, each one of said plurality of wraps secured to said generally planar bandage dispenser substrate and defining a single pocket within which a single one of said individually wrapped sterile bandages resides.

18. The bandage dispenser of claim 1, wherein said each one of said individually wrapped sterile bandages further comprises:
said first adhesive adjacent to said bifurcated end adhering said first sheet to said second sheet and having a strength of said adhering lower than an ultimate tensile strength of both of said first and second sheets and thereby adapted to allow said first sheet to separate from said second sheet and enable access to said sterile bandage; and
a second adhesive distal to said bifurcated end attaching said first sheet to said second sheet, said second adhesive having a strength of said attachment greater than said strength of said adhering and defining a pocket tending to retain said sterile bandage therein.

19. The bandage dispenser of claim 18, wherein said strength of said attachment is greater than an ultimate tensile strength of at least one of said first and second sheets.

20. The bandage dispenser of claim 1, wherein said first sheet and said second sheet further comprise a single unitary sheet having a fold delineating said first sheet from said second sheet, said first and second sheets defining a pocket therebetween.

* * * * *